United States Patent
Bouhour et al.

(10) Patent No.: US 6,397,105 B1
(45) Date of Patent: May 28, 2002

(54) ACTIVE IMPLANTABLE MEDICAL DEVICE HAVING A SOPHISTICATED AUTOMATIC DDD/AAI MODE SWITCHING

(75) Inventors: Anne Bouhour, Ville d'Avray; Jean-Luc Bonnet, Montrouge, both of (FR)

(73) Assignee: ELA Medical, S.A., Montrouge (FR)

( * ) Notice: Subject to any disclaimer, the term of this patent is extended or adjusted under 35 U.S.C. 154(b) by 0 days.

(21) Appl. No.: 09/557,858

(22) Filed: Apr. 26, 2000

(30) Foreign Application Priority Data

Apr. 26, 1999 (FR) .............................. 99 05230

(51) Int. Cl.$^7$ ................................................ A61N 1/18
(52) U.S. Cl. ............................................... 607/9
(58) Field of Search ............................................. 607/9

(56) References Cited

U.S. PATENT DOCUMENTS

| | | | |
|---|---|---|---|
| 5,318,594 A | * 6/1994 | Limousin et al. | 607/9 |
| 5,549,649 A | * 8/1996 | Florio et al. | 607/15 |
| 5,683,426 A | * 11/1997 | Greenhut et al. | 607/9 |
| 5,725,561 A | * 3/1998 | Stroebel et al. | 607/9 |
| 5,836,989 A | * 11/1998 | Shelton | 607/27 |
| 6,122,546 A | * 9/2000 | Sholder et al. | 607/9 |
| 6,129,745 A | * 10/2000 | Sun et al. | 607/27 |

FOREIGN PATENT DOCUMENTS

| | | | |
|---|---|---|---|
| EP | 0 488 904 | 6/1992 | A61N/1/368 |
| WO | 99/10044 | 8/1998 | A61N/1/368 |

* cited by examiner

Primary Examiner—Jeffrey R. Jastrzab
Assistant Examiner—Frances P. Oropeza
(74) Attorney, Agent, or Firm—Orrick, Herrington & Sutcliffe LLP

(57) ABSTRACT

An active implantable medical device having an automatic DDD/AAI mode switching. This device includes sensing spontaneous atrial and ventricular events, detecting an atrio-ventricular block and stimulating the ventricle and atrium, the ventricular stimulation being applied on the detection of an atrio-ventricular block (AVB ), after completion of a programmed atrio-ventricular delay begun on an atrial event. The device also includes a control algorithm that discriminates a paroxystic AVB from a chronic AVB. In the event of an established chronic AVB, the device stops the automatic mode switching, switches to the DDD mode, and reprograms the atrio-ventricular delay with a shorter value than that which previously existed. The AVB discrimination can be based on, in a first phase, a suspicion of a chronic AVB, and in a second phase, a confirmed presence of a chronic AVB in the event that consecutive suspicions of chronic AVB persist for a predetermined length of time.

14 Claims, 1 Drawing Sheet

ACTIVE IMPLANTABLE MEDICAL DEVICE HAVING A SOPHISTICATED AUTOMATIC DDD/AAI MODE SWITCHING

FIELD OF THE INVENTION

The present invention relates to "active implantable medical devices" as defined by the Jun. 20, 1990 Directive 90/385/CEE of the Council of the European Communities, more particularly to pacemaker devices including "multi-site" devices (triple or quadruple chamber), defibrillators and/or cardiovertors, which deliver to the heart low energy pulses for the treatment of heartbeat rate disorders.

BACKGROUND OF THE INVENTION

Implantable devices are known which include stimulation circuits having automatic operation mode switching ("AMS"), as described, for example, in the EP-A-0 488 904 and its counterpart, U.S. Pat. No. 5,318,594, which are assigned to the assignee hereof, ELA Medical, Montrouge, France. More specifically, these devices, which include means for stimulation and detection of the atrium and the ventricle, can operate in one of two modes, for example, DDD and AAI (the AAI mode being a DDD mode including a lengthened atrio-ventricular delay interval), with automatic switching from one mode to the other.

The basic operating mode is typically an AAI mode, with a single chamber atrial simulation. The AAI mode is maintained as long as the atrio-ventricular conduction is normal, i.e., as long as each atrial event (either an atrial detection, corresponding to a spontaneous cardiac activity, or an atrial stimulation) is followed by an associated ventricular detection.

In certain circumstances, for example, during episodes of effort by the patient, atrio-ventricular blocks ("AVB") can appear. These are known as "paroxystic events", involving a depolarization defect of the ventricle. The paroxystic AVB can, however, intervene in circumstances other than those of a patient effort. In these cases, the pacemaker switches automatically into a DDD operating mode with parameters that are optimized for the temporary AVB condition.

To facilitate the return of a spontaneous atrio-ventricular conduction, the pacemaker DDD mode applies a relatively long atrio-ventricular delay (AVD). The AVD length is selected to allow for the patient's spontaneous atrio-ventricular conduction to occur before a stimulation event is applied.

After the disappearance of the AVB condition, and thus re-establishment of a spontaneous AV (atrio-ventricular) conduction, the pacemaker returns automatically to its AAI operating mode once a certain number of known corresponding conditions have been fulfilled, as discussed, e.g., in U.S. Pat. No. 5,318,594.

It has now been discovered that the procedure described above is not well adapted to all types of AVB. Indeed, the switching into a DDD mode with a relatively long AVD, which seeks to support spontaneous AV conduction, is well adapted to a "paroxystic" type AVB, i.e., AVB started by an effort or other external cause, but which condition is temporary in duration. On the other hand, when a patient is subject to a chronic AVB condition, i.e., an AVB that persists over a period of several days, he or she will be stimulated continuously with a long AVD.

However, in this latter circumstance, lengthening of the AVD is not necessary, because it is useless to seek to support a spontaneous AV conduction, as such a spontaneous AV conduction will not likely be expressed. On the other hand, the lengthening of the AVD is potentially harmful because, when in a state of permanent stimulation, the optimal AVD are generally shorter than the spontaneous PR intervals (intervals between an atrial detection P and a ventricular detection R) of patients.

OBJECTS AND SUMMARY OF THE INVENTION

The present invention has for an object to resolve the problems set out above, and improve the operation of the known automatic mode switching implantable active medical devices in the case of AVB conditions.

The present invention is directed to use with a device having an automatic DDD/AAI mode switching as described in EP-A-0 488 904, and U.S. Pat. No. 5,318,594, which includes means for sensing spontaneous atrial and ventricular events; means for detecting an atrio-ventricular block condition preventing spontaneous atrio-ventricular conduction, and means for stimulating the atrium and the ventricle, the ventricular stimulation being applied on the detection of an atrio-ventricular block, after the completion of a programmed atrio-ventricular delay started on a spontaneous or stimulated atrial event.

According to the invention, this device also includes means for discriminating between a paroxystic and a chronic character of an atrio-ventricular block.

In one embodiment, the device additionally advantageously includes means for deactivating the automatic mode switching in the event of a determined chronic atrio-ventricular block, and automatically switching the device into a DDD operating mode and reprogramming the atrio-ventricular delay to have a value shorter than the previously programmed value in this DDD mode.

Preferably, the means for discriminating includes means for determining, in a first phase, a suspicion of a chronic atrio-ventricular block condition, and means for confirming, in second phase, the presence of a chronic atrio-ventricular block in the event of consecutive suspected chronic atrio-ventricular blocks existing for a predetermined time.

In one embodiment, the first phase can be implemented at preset intervals, e.g., daily, and the second phase can be implemented over an interval of several days, optimally over a three-day interval. Thus, in one embodiment, three consecutive days of a suspected chronic AVB condition yields a confirmed AVB condition.

One criterion of suspicion of a chronic atrio-ventricular block that can be used by the discriminating means is the absence of a spontaneous AV conduction during the aforementioned predetermined period, or the absence of a spontaneous conduction after a predetermined number of determined spontaneous conductions, for example, approximately 500 conductions, detected on a daily basis.

A criterion of suspicion of a chronic atrio-ventricular block also can be the application, during the aforementioned predetermined period, of a number, or a percentage, of ventricular stimulation events over a number of cardiac cycles that is higher than a predetermined value, for example, a ventricular stimulation occurring more than 75% of the time, with an atrio-ventricular delay of a duration greater than a certain predetermined value, for example, greater than 200 ms. Other suitable criterion could be used.

BRIEF DESCRIPTION OF THE DRAWING

Further features, characteristics and advantages of the present invention will become more apparent to a person of ordinary skill in the art in view of the following detailed discussion, made with referenced to the attached drawing which is a flowchart of an algorithm that realizes the functions of the invention in a accordance with a preferred embodiment of the invention.

DETAILED DISCUSSION OF THE DRAWING

Figure 1:
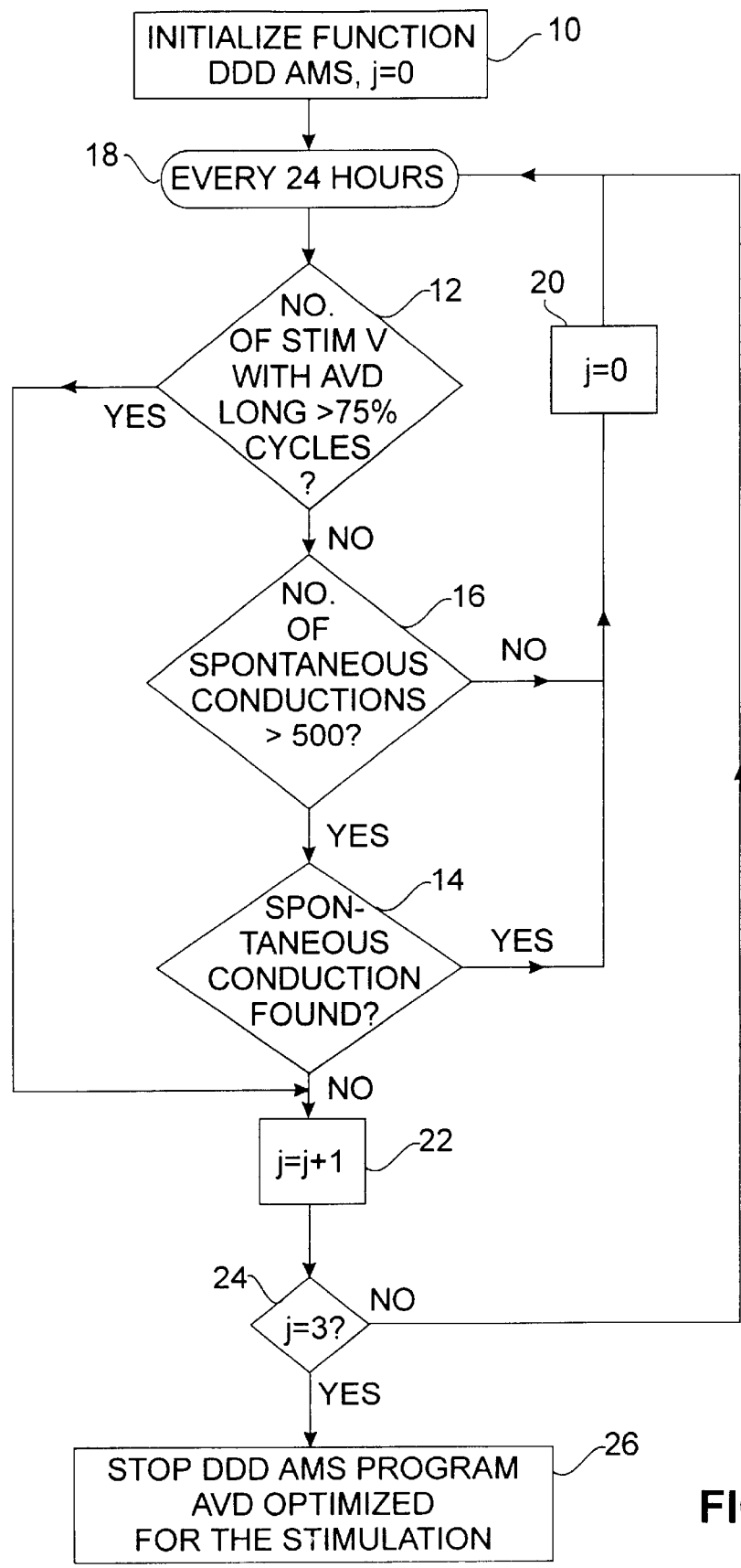

The present invention is preferably implemented in the form of software which executes an automatic mode switching (designated "DDD AMS") control algorithm, operating in a traditional microprocessor controlled-type pacemaker. The CHORUS brand of pacemakers available from ELA Médical are suitable devices, which may be configured with the software at the time of manufacture or by downloading software by telemetry into an already implanted device for implementing the invention.

Initially, the pacemaker, which detects an AVB condition, operates in a DDD mode (stage 10).

The control functions realized by the software implementing the invention initially performs a chronic AVB diagnosis. A chronic AVB is defined as a high degree conduction block, or an AVB I. This diagnosis is typically a two step process. The first step establishes a "suspicion" of a chronic AVB condition, i.e., it functions to determine the possible presence of an AVB condition whose characteristics go beyond a simple paroxystic AVB. More specifically, the algorithm detects the suspected presence of chronic AVB if one of two conditions is met. The first condition is if the ventricle was stimulated with a "long" AVD greater than 200 ms (for example), greater than or equal to 75% (for example) of the cardiac cycles during the preceeding 24 hours (stage 12). The second condition is if no spontaneous conduction was found (stage 14), following the occurrence of spontaneous conduction for the preceding 500 cycles (for example) (stage 16).

This evaluation is operated by increasing the AVD by means of a DDD/ASM algorithm as described in EP-A-0 488 904 and U.S. Pat. No. 5,318,594 mentioned above, and the value of 500 cycles corresponds roughly to a study operated over one half day, taking into account the periods when no evaluation is performed. The first condition is a clinical situation during which one typically wishes to minimize the use of the DDD ASM feature.

This first phase of identifying a suspicion of the AVB diagnosis is undertaken by analyzing the operation of the pacemaker over a standard period, such as a twenty-four hour duration (stage 18). The first phase of suspicion is re-initialized by resetting a day counter j, j=0 (stage 20) if one or more, preferably both, of the two criteria establishing a suspicion is not satisfied.

The various parameters above mentioned are given as examplary (24 hours, 75% of the cycles, 200 ms and 500 cycles), and are programmable with adjustable values according to the patient and the optimization of the diagnosis on a clinical level.

In the second phase, confirming a diagnosis of chronic AVB, the device determines, for example, that a chronic AVB condition in the event that a suspicion of chronic AVB condition exists for three consecutive days (stages 22 and 24). Stage 22 thus increments the day counter j by one day, after each phase of determining if there is a suspicion of a AVB, and stage 24 performs a test of whether j=3 days. If three days have not yet occurred, then the control algorithm is re-initialized at stage 18 for the next day's evaluation.

In the event of an established chronic AVB, the action decided by the device (stage 26) is:

on the one hand, in deactivating the automatic mode switching of the pacemaker, i.e., passing from a DDD/AMS mode to a simple DDD mode, with the AVD no longer being monitored according to spontaneous conduction—which condition is no longer expressed—of the patient, and in addition, reprogramming the AVD (both its length and hysteresis values) with values optimized for permanent stimulation. These reprogrammed values generally correspond to pre-programmed values of the device, but are shorter in duration.

One skilled in the art will appreciate that the present invention can be practiced by other than the embodiment disclosed, which are presented for purposes of illustration, and not of limitation.

We claim:

1. An active implantable medical device having a DDD operating mode and an AAI operating mode and an automatic DDD/AAI mode switching including:

means for sensing spontaneous atrial and ventricular events including an atrio-ventricular conduction;

means for detecting an atrio-ventricular block preventing a spontaneous atrio-ventricular conduction;

means for providing a programmed atrio-ventricular delay in response to one of an atrial stimulation and a sensed spontaneous atrial event; and means for ventricular and atrial stimulation, said ventricular stimulation being applied in response to a detection of an atrio-ventricular block following said provided programmed atrio-ventricular delay, wherein the improvement comprises:

means for discriminating between an atrio-ventricular block having a paroxystic character and a chronic character.

2. The device of claim 1, further comprising means, responsive to a discriminated chronic atrio-ventricular block, for deactivating the automatic mode switching and switching said device to operate in said DDD mode.

3. The device of claim 2 further comprising means for reprogramming permanently the atrio-ventricular delay in response to said discriminated chronic atrio-ventricular block.

4. The device of claim 3 wherein said reprogrammed atrio ventricular delay has a value shorter than the prior programmed atrio-ventricular delay.

5. The device of claim 1, wherein the means for discriminating further comprises:

means for suspecting a chronic atrio-ventricular block condition as a function of a suspicion criteria, and means for confirming the chronic atrio-ventricular block in response to a suspected chronic atrio-ventricular block existing for a predetermined length of time.

6. The device of claim 5, further comprising means for operating the suspecting means on a daily interval, and wherein the predetermined length of time is a pluri-day interval.

7. The device of claim 6, wherein the pluri-day interval further comprises a three day interval.

8. The device of claim 5, wherein the suspicion criteria further comprises an absence of a spontaneous atrio-ventricular conduction during said-programmed atrio-ventricular delay.

9. The device of claim 5, wherein the suspicion criteria further comprises an absence of a spontaneous atrio-ventricular conduction after a predetermined number of spontaneous conduction evaluation cycles.

10. The device of claim 9, wherein said predetermined number is 500.

11. The device of claim 5, wherein the suspicion criteria further comprises an application, during the aforementioned atrio-ventricular delay, of a ventricular stimulation for a number or a percentage of cardiac cycles that is higher than a first predetermined value with an atrio-ventricular delay having a duration higher than a second predetermined value.

12. The device of claim 11, wherein said suspicion criteria further comprises an absence of a spontaneous atrio-ventricular conduction after a predetermined number of spontaneous conduction evaluation cycles.

13. The device of claim 12, wherein said predetermined number is 500.

14. The device of the claim 11, wherein the first aforementioned predetermined value is 75% and the second aforementioned predetermined value is 200 ms.

* * * * *